//; United States Patent
Bob (10) Patent No.: US 11,771,490 B2
(45) Date of Patent: Oct. 3, 2023

(54) BLADE CARTRIDGE FOR A SURGICAL INSTRUMENT (71) Applicant: Erbe Elektromedizin GmbH, Tuebingen (DE)

(72) Inventor: Felix Bob, Rottenburg (DE)

(73) Assignee: ERBE Elektromedizin GMBH, Tuebingen (DE)

( * ) Notice: Subject to any disclaimer, the term of this patent is extended or adjusted under 35 U.S.C. 154(b) by 15 days.

(21) Appl. No.: 17/715,346

(22) Filed: Apr. 7, 2022

(65) Prior Publication Data

US 2022/0331002 A1 Oct. 20, 2022

(30) Foreign Application Priority Data

Apr. 19, 2021 (EP) ..................................... 21169197

(51) Int. Cl.
*A61B 17/3213* (2006.01)
*A61B 18/14* (2006.01)
*A61B 17/285* (2006.01)
*A61B 17/00* (2006.01)
*A61B 18/00* (2006.01)
*A61B 17/295* (2006.01)
*A61B 17/3215* (2006.01)

(52) U.S. Cl.
CPC ...... *A61B 18/1442* (2013.01); *A61B 17/3213* (2013.01); *A61B 17/285* (2013.01); *A61B 17/295* (2013.01); *A61B 17/3215* (2013.01); *A61B 2017/0023* (2013.01); *A61B 2017/00477* (2013.01); *A61B 2018/00589* (2013.01); *A61B 2018/1455* (2013.01)

(58) Field of Classification Search
CPC . A61B 17/28; A61B 17/2812; A61B 17/2841; A61B 17/285; A61B 17/3213; A61B 2017/0023; A61B 2017/00477; A61B 2018/146
See application file for complete search history.

(56) References Cited

U.S. PATENT DOCUMENTS

| | | | |
|---|---|---|---|
| 8,858,547 B2 * | 10/2014 | Brogna | A61B 18/1445 606/49 |
| 2010/0292691 A1 | 11/2010 | Brogna | |
| 2011/0004208 A1 | 1/2011 | Truckai et al. | |
| 2020/0375653 A1 * | 12/2020 | Bob | A61B 18/1442 |
| 2020/0375654 A1 * | 12/2020 | Bob | A61B 18/1442 |
| 2021/0121193 A1 * | 4/2021 | Bob | A61B 17/320092 |
| 2022/0142698 A1 * | 5/2022 | Bob | A61B 18/085 |
| 2022/0304742 A1 * | 9/2022 | Kaupp | A61B 18/1442 |
| 2022/0331002 A1 * | 10/2022 | Bob | A61B 17/3213 |

* cited by examiner

*Primary Examiner* — Ryan J. Severson
(74) *Attorney, Agent, or Firm* — Blank Rome LLP (57) ABSTRACT A knife cartridge for use in a surgical instrument. The knife cartridge includes a blade that can be operated by a second operating element. The blade is held in a blade housing that can be transferred from a first locking position (passive position) into a second locking position (active position) by a first operating element. In the passive position the blade housing is completely located inside the cartridge housing and the blade is locked therein. In the active position the blade housing projects out of the cartridge housing. Only in the active position a locking between the blade housing and blade can be released, whereby also only then a driving connection is established between the second operating element and the blade.

15 Claims, 7 Drawing Sheets

BLADE CARTRIDGE FOR A SURGICAL INSTRUMENT

CROSS-REFERENCE TO RELATED APPLICATION

This application claims priority to European Application No. 21169197.7, filed Apr. 19, 2021, the entirety of which is incorporated by reference herein.

TECHNICAL FIELD

Embodiments of the invention described herein relate to a knife cartridge for a surgical instrument.

BACKGROUND

Surgical instruments, particularly for the open surgical use, are frequently configured in the type of forceps or scissors. For example, US 2011/0004208 A1 discloses such an instrument for fusioning and cutting of vessels. The two jaws of this forceps-like instrument that are movable relative to each other are provided with coagulation electrodes. In addition, a holder for a knife cartridge is provided on the instrument that comprises a blade for cutting fusioned blood vessels. The knife cartridge can be exchanged in order to again provide the instrument with a sharp blade, if the blade has become blunt. In addition, the possibility of use of single-use knives on a sterilizable instrument or instrument that can be reused multiple times is opened.

SUMMARY

In the sterilizable instrument for guidance of the knife blade of an exchangeable cartridge a knife channel is provided that can contaminate during use of the instrument and is difficult to access for cleaning. However, dangers for patients due to infectious material that remains in the instrument have to be excluded.

It is the object of embodiments of the invention to provide a measure how the safety for patients and/or personnel can be improved during use of respective instruments.

This object is solved, for example, by means of a knife cartridge, but can be connected with a surgical instrument.

The knife cartridge can be used on a forceps-like instrument that is configured to cut tissue by means of a blade held between two jaws. The blade is movably supported in a blade housing; the blade housing in turn is movably supported in the cartridge housing. This concept allows to first extend the blade housing together with the blade supported therein in a protected manner up to the tissue held between the jaws in order to only then move the blade out of the blade housing in order to cut the tissue. If the blade is retracted into the blade housing after termination of the cut, it can carry tissue adherences and thus can contaminate the blade housing inside. However, a channel provided in the instrument through which the blade housing is moved out of the cartridge housing up to the jaws holding the tissue remains clean. Each part that has been in contact with the tissue is retracted into the blade housing and if applicable together therewith into the cartridge housing and is disposed together with the cartridge housing after use. Each part getting into contact with the knife channel of the instrument, namely the blade housing, does not get into contact with the tissue. In doing so, the knife cartridge according to embodiments of the invention simplifies the cleaning and sterilization of the surgical instrument. In addition, a possible wear of the instrument is reduced, because the sharp blade is not guided and moved in the knife groove of the instrument, but in the blade housing. Due to this concept the safety for patients is increased.

The blade housing can be made of metal or also a plastic or a combination thereof. The blade housing can be configured as rectangular tube surrounding the blade or as rail and can be flexibly deformable. Thus, it can be moved also through an arc-shaped groove in the instrument while being flexibly deformed.

The knife cartridge according to embodiments of the invention guides the blade inside the blade housing to its location of use, i.e. up to the tissue held between the jaws. Thereby the blade housing can be moved in a groove provided in the instrument, e.g. through the hinge area of the instrument. The blade and particularly the cutting edge thereof are protected. Neither the cutting edge can touch along parts of the instrument and getting blunt thereby nor can it create scratches or the like on such instrument parts in which contamination could remain. This increases the patient safety.

The knife cartridge is preferably provided with latching means that allow a releasable attachment of the cartridge housing on the instrument. The latching means can be transferred from a latching position in a release position by means of a separate operating element. Alternatively, the latching means can also be operated by the first operating element by means of which the blade housing can be moved. The operation is thus simple and intuitive.

The blade housing preferably comprises a first locking position in which the blade housing is completely positioned inside the cartridge housing. An insertion feeler provided on the cartridge housing can be configured to block an operation of the first operating element and/or a movement of the blade housing out of the first locking position. The insertion feeler serves to block the movement of the blade housing, if the knife cartridge is located outside an instrument. The insertion feeler in addition serves to release a movement of the blade housing, if the knife cartridge is inserted into the instrument.

The insertion feeler is preferably a movably supported blocking member that is spring elastically supported and movable between a blocking position and a release position. In the blocking position it blocks a movement of the blade housing out of its first locking position (rest position). Thereby the insertion feeler is preferably arranged such that it is urged out of its blocking position against the force of its spring in a release position by means of an abutment surface of the instrument, if the knife cartridge is coupled to the instrument. Only then a movement of the blade housing is released. In doing so, the blade and its blade housing are immovably held in the cartridge as long as the knife cartridge is not inserted into the instrument. They can also not be moved out of the cartridge housing by clumsy handling. Injuries of the handling personnel, transmission of infections or the like are thus largely excluded.

If the cartridge housing is coupled to the instrument and if the insertion feeler thus releases the movement of the blade housing, it can be transferred by operation of the first operating element in a second locking position (active position) in which the blade housing projects out of the cartridge housing.

Typically the instrument comprises a channel that extends from a cartridge seat arranged proximal to the scissors joint of the instrument up to the knife slit configured in the jaws of the instrument. In the second locking position the knife housing is moved forward up to the knife slit. During movement of the blade housing out of the first locking position into the second locking position and back, the blade is fixedly (immovably) coupled with the blade housing. This coupling can be eliminated in the second locking position by means of a respective release movement of the first operating element, whereby an axial movement of the blade relative to the blade housing is then released also. The release is carried out by means of a transfer device that concurrently drivingly connects the blade with the second operating element during separation of the operating element from the blade. The second operating element can now be used to move the blade out of the blade housing and thereby cut biological tissue, for example. The transfer device can also be denoted as "switch" that is configured to alternatively drivingly connect the first or the second operating element with the blade. Thereby the switch concurrently connects the first operating element with the blade housing and the blade. If the switch is changed, the switch connects the second operating element exclusively with the blade.

An operation lock can be effective between the first operating element and the second operating element that releases an operation of the second operating element for movement of the blade only, if the transfer device (switch) has been activated by means of a respective movement of the first operating element, whereby the blade is decoupled from the blade housing and concurrently the second operating element is coupled with the blade. This concept can also be used in embodiments of the knife cartridge without blade housing or with a short blade housing that remains completely in the knife cartridge from which the blade already projects or exits while it is still moved distally.

A movement lock can be assigned to the first operating element that blocks a movement and thus a displacement of the blade housing inside the cartridge housing as long as the transfer device allows a driving connection between the second operating element and the blade and no driving connection exists between the first operating element and the blade.

It is in addition possible to use the first operating element for releasing the latching connection between the knife cartridge and an instrument. For this purpose the latching means provided on the cartridge housing can comprise a cam with which a latching member can be moved against the force of a spring in a release direction. Also the first operating element can be provided with a cam that can be moved against the cam of the latching member due to a respective force application of the first operating element.

With the mechanism described in this manner, it is guaranteed that the blade can only be moved out of the cartridge housing and the blade housing, if the knife cartridge is correctly connected with the instrument and the blade housing is transferred into the active position. In the active position the blade housing is located with its face at the location of use of the blade. The distance between the cartridge housing and the location of use of the blade is bridged by means of the blade housing. The location of use of the blade is located distally relative to a hinge joint of the instrument while the knife cartridge is proximally arranged relative to this joint. The channel provided in the instrument for arranging of the blade housing is not contaminated or contaminated in a minor manner due to the proposed configuration.

The cartridge housing can only be removed from the instrument, if the blade is retracted in the blade housing and the blade housing is retracted in the cartridge housing. An unlocking of the cartridge housing from the instrument, i.e. a release therefrom, is only possible if the blade housing is completely retracted into the cartridge housing. After the release of the cartridge housing from the instrument neither the blade housing nor the blade can be moved out of the cartridge housing. The blade housing and the blade are arrested inside the cartridge housing. The cutting edge of the blade remains in each case inaccessibly arranged inside the knife cartridge.

BRIEF DESCRIPTION OF THE DRAWINGS

Further advantageous details are derived from the claims as well as the drawing with its figures and the respective description. The drawings show:

DETAILED DESCRIPTION

Figure 1:
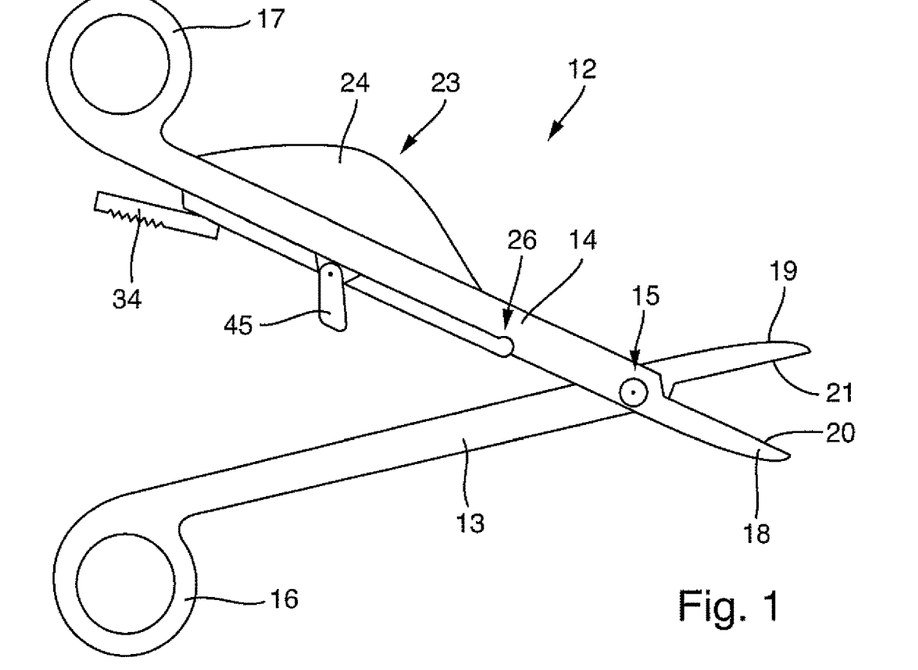
FIG. 1: an instrument having a knife cartridge according to an embodiment of the invention in a side view in basic illustration.

A surgical instrument 12 having two legs 13, 14 is illustrated in FIG. 1 that are pivotably connected with one another in the type of a forceps or scissors by means of a joint 15. At their proximal ends the legs 13, 14 comprise handles 16, 17. At their distal ends legs 13, 14 are jaws 18, 19 between which biological tissue can be held and compacted. For example, the tissue can be blood vessels, other hollow vessels or also tendons, skin, muscles or the like. The jaws 18, 19 can be configured in a smooth or slightly profiled manner. In addition they can be made of an electrically conductive or electrically non-conductive material. If the surfaces 20, 21 of the jaws 18, 19 that face each other are configured in an electrically conductive manner, they can be configured as an electrode, for example, in order to subject tissue held between the jaws 18, 19 to a current flow and to coagulate and/or fusion tissue. The surfaces 20, 21 facing one another thus form electrodes to which current can be supplied via a not further illustrated cable or also a voltage source provided on the instrument. In addition, further elements, such as switches or the like, can be provided in order to control the current flow, particularly switch it on and off.

Figure 3:
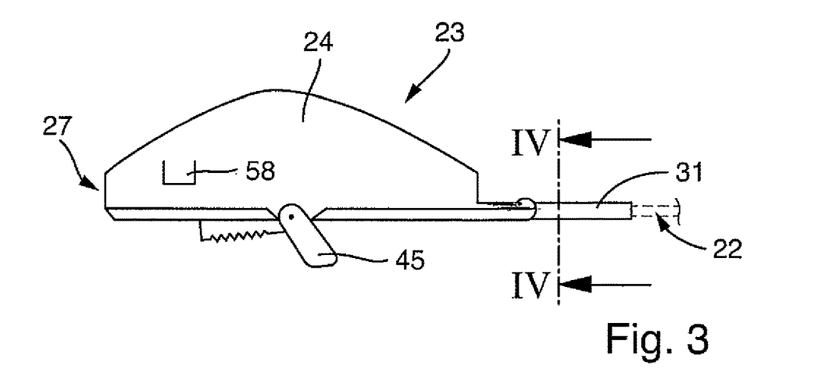
FIG. 3: a knife cartridge according to FIG. 2 with its blade housing being in an active position and a blade that can be extended (extended in dashed illustration)

The instrument 12 is preferably a coagulation and cutting instrument that uses a blade (FIG. 3, FIG. 4, FIG. 6) for cutting of tissue. The blade 22 is part of a knife cartridge 23 that is releasably held on the instrument 12. For example, the leg 14 comprises a seat for this purpose, e.g. configured as compartment, in which the knife cartridge 23 can be inserted. The knife cartridge 23 is preferably configured for single use while the instrument 12 is configured as sterilizable instrument 12 that can be reused multiple times. While the knife cartridge 23 is separated from the instrument and disposed after use, the instrument 12 is subject to cleaning and sterilization.

The knife cartridge 23 comprises a cartridge housing 24 that can be configured as plastic injection molding part, for example. At its in use distal end it is provided with a coupling structure 25 that fits into a respective complementary structure of the leg 14. For example, the coupling structure can be a bead-like projection that fits into a respective shaped transverse groove 26 of instrument 12. At its opposite proximal end cartridge housing 24 can comprise a latching means 27, a latching member 28 can be part thereof arranged inside the cartridge housing 24 and being pivotably supported, for example. The latching member 28 can cooperate with a latching projection 29 of instrument 12 that latches into the latching member 28 as soon as the cartridge housing 24 is moved toward leg 14 by means of pivot movement around a transverse axis defined by transverse groove 26. The coupling structure 25 and the transverse groove 26 thereby form a pivot hinge. A spring 29, e.g. in the form of a pressure spring, bendable flexible spring, leaf spring or the like, can be part of the latching means 27. The spring means 29 can be a monolithic part of the latching member 28 or can be a flexible tongue configured on the cartridge housing 24 in the interior or also a separate spring element. Inside the cartridge housing 24 the latching member 28 is movable by means of a pivot bearing 30, for example slideably or also pivotably held.

Figures 4, 5:
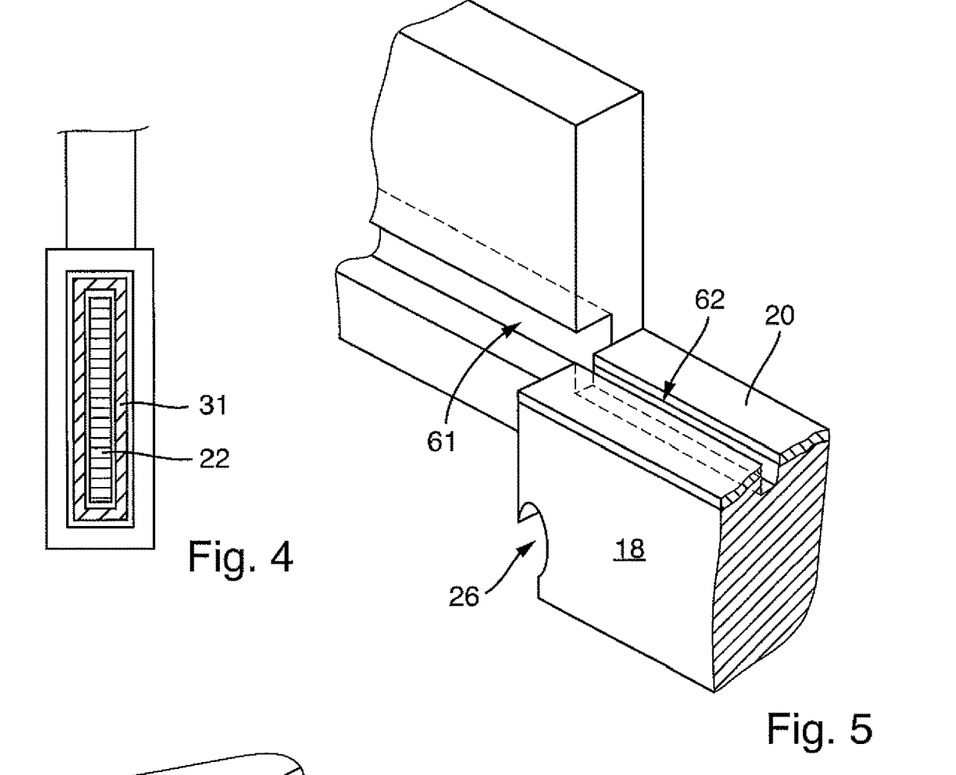
FIG. 4: the knife cartridge according to FIG. 3 cut along line IV-IV.
FIG. 5: a part of the instrument according to FIG. 1 without a knife cartridge in a highly enlarged schematic perspective illustration.
Figure 6:
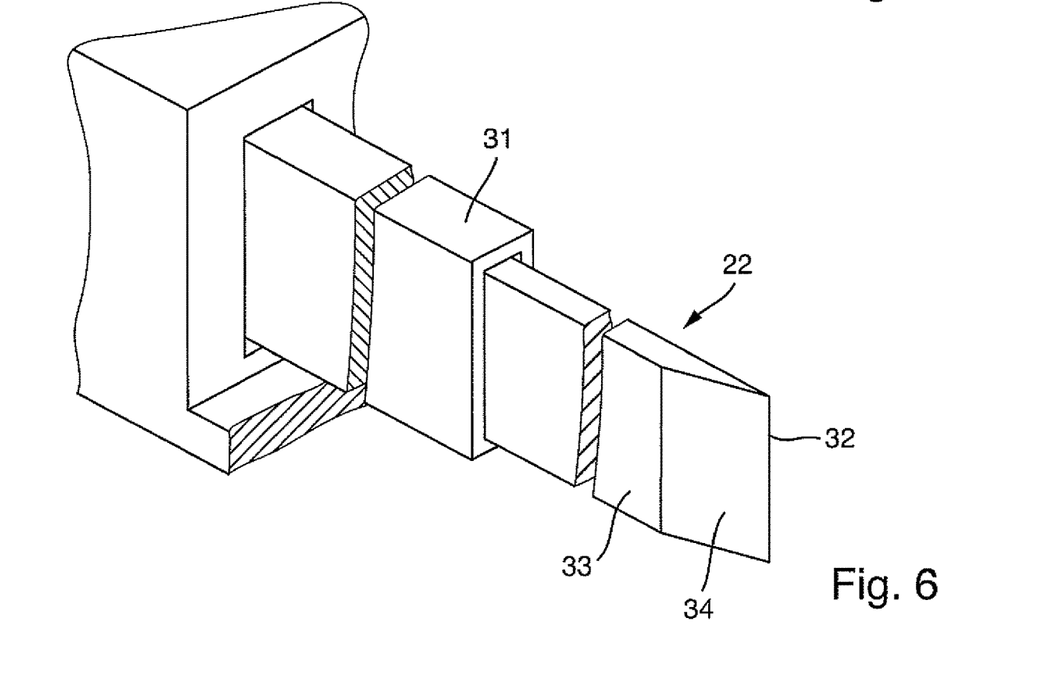
FIG. 6: the knife cartridge according to FIG. 3 in a sectional perspective and highly shortened illustration.

In addition, a blade housing 31 is arranged inside the cartridge housing 24 that can be configured as flat rectangular tube or also as flat guiding rail, preferably of metal or else also of plastic. Reference is particularly made to FIGS. 4 and 6 that illustrate that at least the front part of the blade housing 31 that can be moved out of the cartridge housing surrounds the flat blade 22 at the two flat sides as well as the top and bottom narrow sides. However, the blade housing 31 can be open on the top narrow side, at least along a part of its length, particularly its proximal part that always remains inside the cartridge housing 24. There an extension 22a of the blade 22 can project out of the blade housing 31.

Blade housing 31 can be open in sections also on one of the flat sides. The blade housing 31 can be open on a side, for example, that faces away from a cutting edge 32 of blade 22. As illustrated in FIG. 6, the cutting edge 32 can be arranged out of the center relative to the blade 22 and can directly adjoin one flat side surface of blade 22. The other side surface 33 then transitions into an oblique surface 34 that extends up to the cutting edge 32. Preferably the blade housing 31 is configured so long that the blade 22 is completely located in the blade housing 31 in retracted position. Thereby the cutting edge 32 is located inside the blade housing 31. It is however also possible to configure the blade housing in a shortened manner, such that the blade 22 always slightly projects out of the blade housing and the cutting edge 32 is located in front of the distal end of the blade housing 31. In addition, embodiments without blade housing exist.

Figure 7:
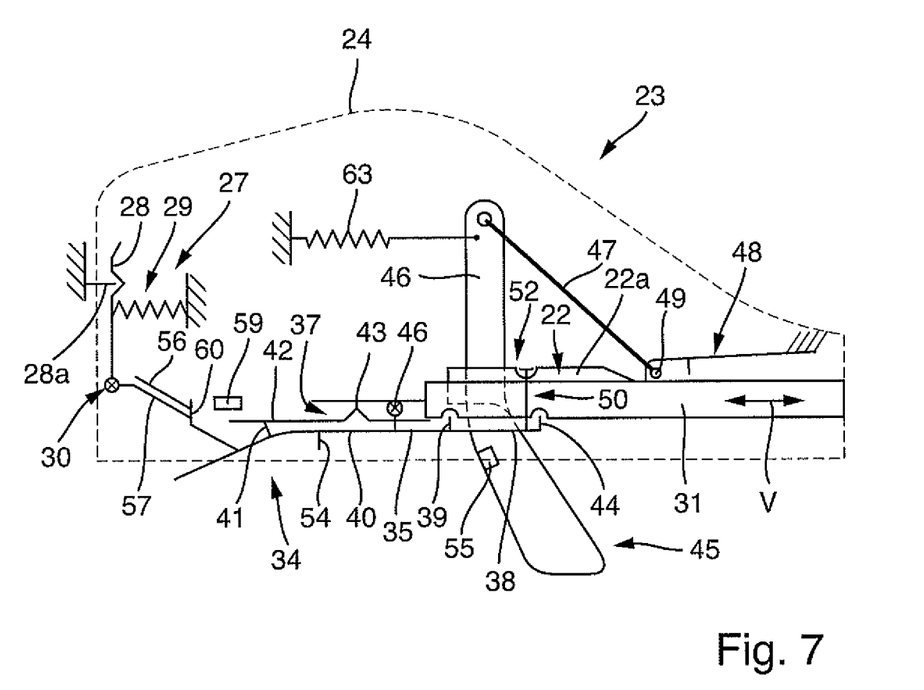
FIG. 7-11: the knife cartridge according to FIGS. 2 and 3 in different positions and conditions in an illustration of the kinematic principle.
Figure 8:
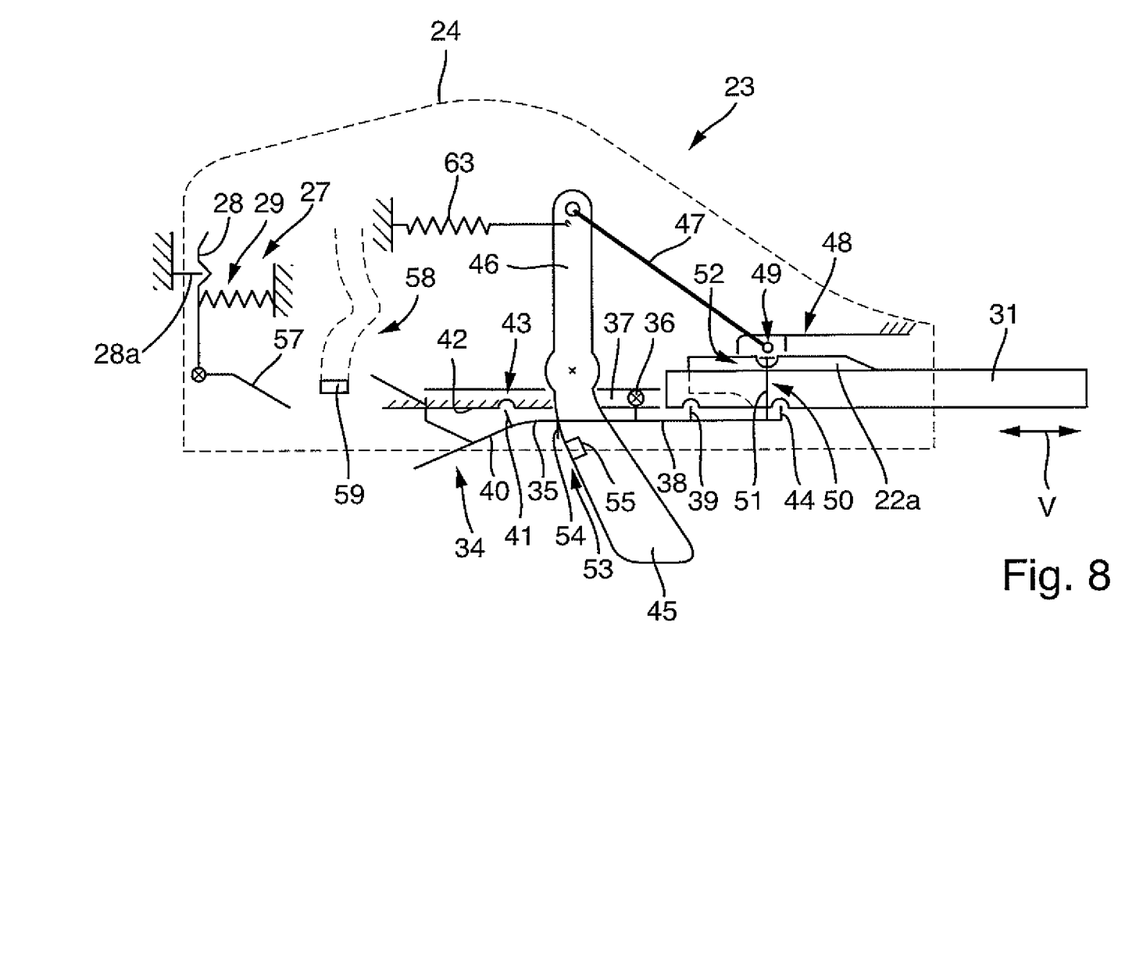

A blade housing 31 is basically movably arranged inside the cartridge housing 24 and guided in a movement direction V (FIG. 7, FIG. 8). Thereby the blade housing 31 can be transferred from a first locking position according to FIG. 7 in a second locking position according to FIG. 9. In the first locking position the blade housing 31 is completely located inside the cartridge housing 24. In the second locking position according to FIG. 8 and FIG. 9 (active position) the blade housing 31 projects from the distal end of the cartridge housing 24.

Figure 9:
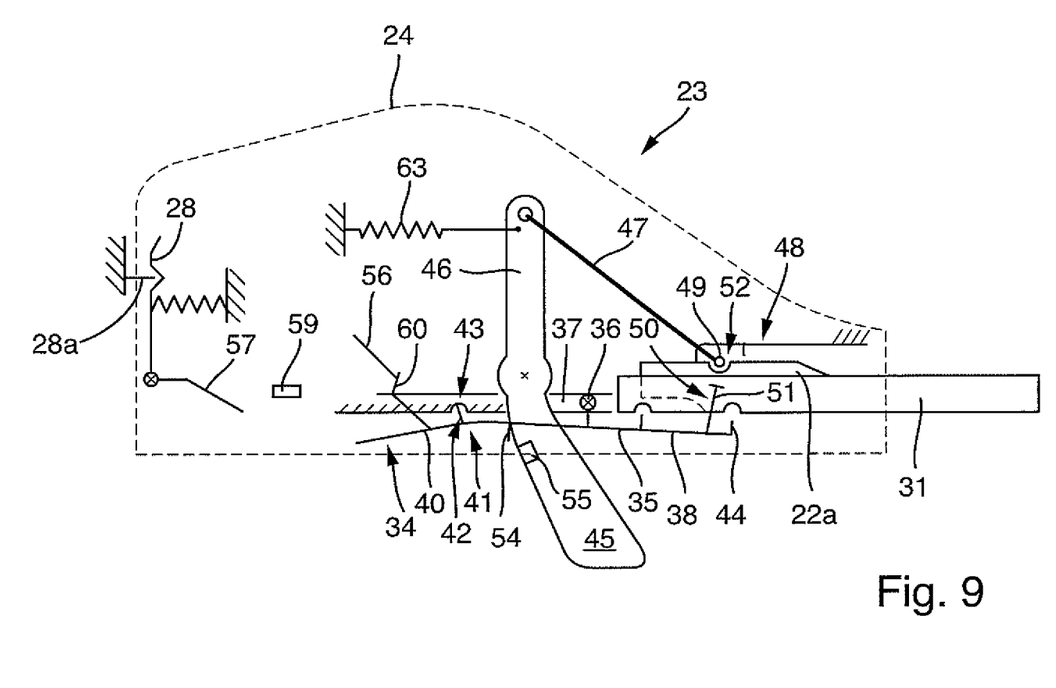

A first operating element 34 serves for movement of blade housing 31 out of the first locking position into the second locking position according to FIGS. 8 and 9, whereby a pivot and locking rocker 35 is part of the first operating element 34. This pivot and locking rocker 35 forms a two-arm lever, the first arm 38 of which is connected with the blade housing 31 in order to transfer a movement in movement direction V on the blade housing 31. For this the arm 38 can be provided with a projection 39 that extends into a cavity of the blade housing 31.

The pivot and locking rocker 35 comprises a second arm 40 on which the first operating element 34 can be held. The operating element 34 is preferably rigidly connected with the pivot and locking rocker 35. In addition, one of the arms 38, 40, preferably arm 40, is provided with a pivot and movement lock 41 that can be configured as cam or projection, for example. It slides along a locking surface 42 during movement of the pivot and locking rocker 35 in movement direction V that is arranged such that a pivot movement of the pivot and locking rocker 35 is blocked. However, the locking surface 42 comprises a cavity 43 that is arranged opposite the pivot and movement lock 41, if the pivot and locking rocker 35 is positioned in its second locking position, i.e. the distally maximum extended position (active position), as illustrated in FIGS. 8 and 9.

Figure 11:
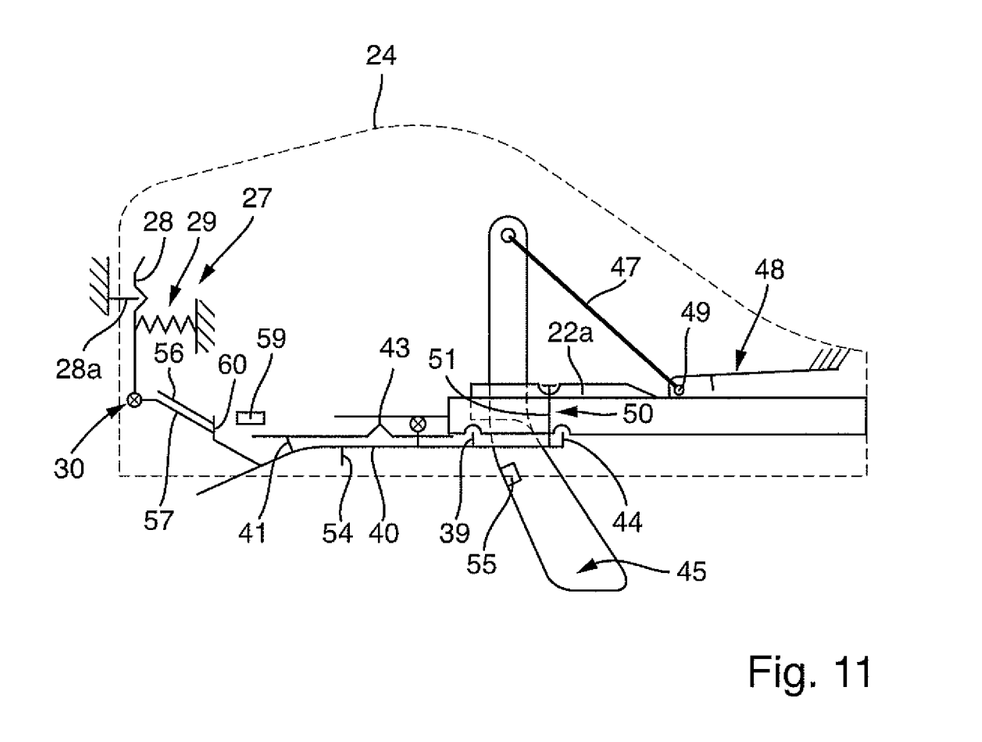

In addition, first arm 38 supports a coupling 44 that establishes an immovable connection in movement direction V between the first arm 38 and blade 22 through an opening in the blade housing 31. For this purpose blade 22 comprises cavity at its location facing the coupling 44 into which a projection of arm 38 extends, which projection forms the coupling 44. Thus, blade 22 is immovably coupled in movement direction V with the blade housing 31 by means of the projection 39 and the coupling 44 as long as the pivot and locking rocker 35 is in a non-pivoted position, i.e. as long as the pivot and movement lock 41 does not extend into cavity 43 (FIGS. 7, 8 and 11).

Figure 2:
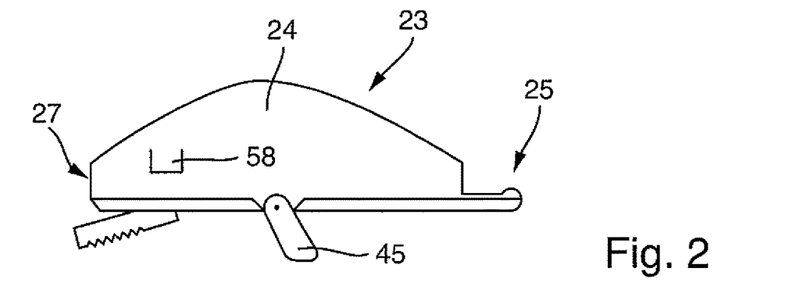
FIG. 2: the knife cartridge according to FIG. 1 in a dashed illustration in a handable condition in a side view.

For operating blade 22, i.e. for extending out of the blade housing 31, a second operating element 45 is provided that is preferably a two-arm lever being pivotably supported on cartridge housing 24. The pivot axis of the second operating element 45 is preferably orientated transverse to the movement direction V. The second operating element 45 thereby projects from cartridge housing 24, as particularly shown in FIGS. 1-3. However, if the knife cartridge 23 is connected with leg 14 of instrument 12, operating element 45 projects in direction toward the other leg 13 and passes it due to lateral offset, if instrument 12 is closed.

A lever arm 46 of second operating element 45 arranged in the cartridge housing 24 can be coupled with blade 22 by means of a connecting rod 47. For this purpose the blade 22 comprises an extension 22a projecting out of the blade housing 31 that is configured as ramp at its distal end. On this extension 22a a bar 48 is supported that can be a spring elastic arm held on the cartridge housing 24 having a forked end. In the forked end of bar 48 a coupling pin 49 can be located arranged on an end of connecting rod 47.

The pivot and locking rocker 35 supports a transfer mechanism 50 on its distal end of arm 38. It is realized by an extension 51 of arm 38 that extends originating from arm 38 adjacent to a coupling cavity 52 formed in the extension 22a, thereby passing the blade housing 31. The extension avoids entering of coupling pin 50 into coupling cavity 52 as long as pivot and locking rocker 35 is in a non-pivoted position, i.e. pivot and movement lock 41 does not engage into cavity 43. If lever arm 38 of pivot and locking rocker 35 is pivoted upward (FIG. 8), coupling 44 engages in blade housing and the extension 51 urges coupling pin 49 out of the cavity 52. If lever arm 38 pivots downward (FIG. 9), coupling pin 49 latches into the cavity 52. Thus, the transfer mechanism 50 ensures that blade 22 is either coupled with the first operating element 34 and the blade housing 31 or else with the second operating element 45.

In addition, an operation lock 53 is effective between pivot and locking rocker 35 and the second operating element 45 (FIG. 8) that temporarily blocks operation of the second operating element 45. The lock is effective, if the blade housing 31 is in expanded position, i.e. in active position. Thus, the lock is effective as long as the pivot and locking rocker 35 is still coupled with blade 22. A respective projection 54 of pivot and locking rocker 35 releases the path for a projection 55 of second operating element 45, only if the rocker 35 is tilted, such that pivot and movement lock 41 engages into cavity 43 and the coupling 44 is decoupled and the blade 22 are released. This condition is illustrated in FIG. 9. Now connecting rod 47 establishes the driving connection between the second operating element 45 and blade 22 that then can be moved out of the blade housing 31 by means of operation of second operating element 45.

The second arm 40 is in addition connected with a wedge or cam 56 that is connected with a wedge or cam 57 of latching member 28. The cams 56 and 57 are positioned such that they get into engagement, if pivot and locking rocker 35 is in its proximal extreme position.

The cartridge housing 24 can in addition comprise an insertion feeler 58 that can be realized as spring elastic tongue configured on the cartridge housing 24 and slightly projecting beyond the outer contour thereof. This spring elastic tongue comprises a bottom end that is movable transverse to the movement direction V. This bottom end can be configured as stop block 59 to which a stop surface is assigned that is configured on the lever arm 40. It is arranged such that a substantial movement of pivot and locking rocker 35 out of the proximal position is impossible as long as insertion feeler 58 is not urged out of its rest position.

The knife cartridge 23 described so far operates as follows:

FIG. 7 illustrates the knife cartridge 23 in delivered condition in which it can be safely handled. Blade 22 is completely retracted into blade housing 31 and secured therein. Blade housing 31 is completely positioned inside cartridge housing 24 and locked therein. The first operating element 34 is in proximal position. An operation of second operating element 45 does not results in a change of this situation. Neither can blade 22 be moved out of blade housing 31 nor can blade housing 31 be moved out of cartridge housing 24.

Knife cartridge 23 can be connected to instrument 12, whereby latching member 28 gets into engagement with a respective latching projection 28a that can be configured on the instrument 12. Concurrently an element of instrument 12, e.g. a surface provided on leg 14, urges insertion feeler 58 against its spring effect slightly in direction toward the interior of cartridge housing 24. Provided that insertion feeler 58 projects beyond the contour of the cartridge housing 24, it is urged inside the contour of the cartridge housing 24, for example. In doing so, stop block 59 releases a movement of the first operating element 34 in distal direction (to the right in FIG. 7). The operator can now move the first operating element 34 in distal direction. Thereby the blade housing 31 and the blade 22 locked therein are moved in movement direction V distally out of the cartridge housing 24, as illustrated in FIG. 8. The blade housing 31 thereby moves forward up to the jaw 18 inside a channel 61 (FIG. 5) provided for this purpose.

The channel 61 can extend through the region of joint 15. It ends at jaw 18 at a knife slit 62 and preferably abuts with its face against the inlet of knife slit 62. During forward movement of blade housing 31 inside channel 61 the cutting edge 32 of blade 22 is located in blade housing 31 and protected.

Figure 10:
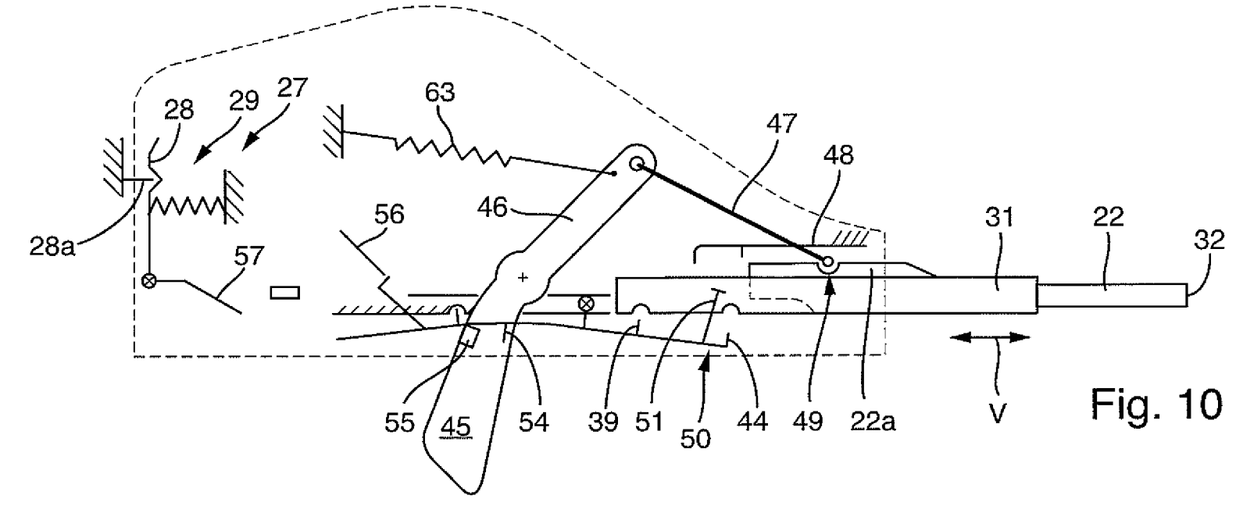

The pivot and locking rocker 35 still locks blade 22 in the blade housing 31 while operating element 34 is moved in distal direction. During this process a decoupling of blade housing 31 and blade 22 is impossible, because pivot and movement lock 41 moves along locking surface 42 and prevents pivot movement of pivot and locking rocker 35. Only in the maximum distal position, i.e. the second locking position of blade housing 31, the pivot and movement lock 41 is positioned in front of cavity 43, as illustrated in FIG. 8. Now a pivot movement of pivot and locking rocker 35 is released. The operator can now press first operating element 34 toward the cartridge housing 24 and thereby slightly pivot the pivot and locking rocker 35. As apparent from FIG. 9, coupling 44 thereby leaves blade housing 31 and thereby also decouples from blade 22. Concurrently the transfer mechanism 50 releases coupling cavity 52 such that coupling pin 49 can enter into coupling cavity 52 of blade 22. Also projection 54 releases projection 55 such that the second operating element 45 can now be operated, i.e. pivoted, as illustrated in FIG. 10.

If second operating element 45 is operated (pivoted in clockwise direction in the figures), it moves the blade 22 in movement direction V, i.e. distally out of blade housing 31, by means of its connecting rod 47. The blade 22 enters into knife slit 62 and cutting edge 32 moves along inside knife slit 62 (FIG. 5). For example, blade 22 can cut tissue held between jaws 18, 19. The knife slit can thereby be straight or also curved, if the blade 22 is sufficiently flexible. Preferably the blade 22 is thereby configured such that cutting edge 32 is arranged on the side of the convex flank of knife slit 62.

If second operating element 45 is released, a respective return spring 63 retracts operating element 45 back in its rest position. In doing so, blade 22 is concurrently retracted back into blade housing 31 by means of connecting rod 47. Starting from the condition according to FIG. 10, the condition of FIG. 9 is reached again in this manner. The instrument 12 and the knife cartridge 23, however, remain operable. The operating element 45 can be operated repeatedly, whereby blade 22 extends and retracts again and again.

If the knife cartridge 23 shall be removed from instrument 12, first the second operating element 45 is released such that the condition according to FIG. 9 is established. Subsequently, the first operating element 34 is pivoted away from cartridge housing 24 downwardly, such that coupling 44 engages into blade housing 31. Thus, blade 22 is immovably locked inside the still expanding blade housing 31. Now an operation of the second operating element is no longer possible, because the projection 54 provided on the pivot and locking rocker 35 blocks the path of projection 55 provided on the second operating element 45. The transfer mechanism 50 thereby lifts pin 49 of connecting rod 47 out of the coupling cavity 52. In doing so, the second operating element 45 is now decoupled from blade 22.

The first operating element 34 is subsequently moved in proximal direction, i.e. to the right in FIG. 8, so that it reaches the position according to FIG. 7. Pin 49 of connecting rod 47 exits extension 22a of blade 22. Due to the pivot and movement lock 41 that moves along locking surface 42, the pivot and locking rocker 35 can thereby not be pivoted such that the rigid coupling between blade 22 and blade housing 31 cannot be released.

If now knife cartridge 23 shall finally be released from instrument 12, the first operating element 34 is urged beyond its proximal end position illustrated in FIG. 7 in proximal direction, as illustrated in FIG. 11. Thereby cam 56 abuts against cam 57 such that latching member 28 is pivoted against the force of spring 29. The latching means 27 is thus released and the knife cartridge 23 can be removed from instrument 12.

In all embodiments of knife cartridges 23 without blade housing 31 the above description applies accordingly, however, under the provision that the blade housing 31 and as an option also the projection 39 are omitted.

A knife cartridge 23 according to embodiments of the invention is provided for use in a surgical instrument 12. The knife cartridge 23 comprises a blade that can be operated by means of a second operating element 45. The blade 22 is held in a blade housing 31 that can be transferred from a first locking position (passive position) into a second locking position (active position) by means of a first operating element 34. In the passive position the blade housing 31 is completely located inside the cartridge housing 24 and the blade 22 is locked therein. In the active position the blade housing 31 projects out of the cartridge housing. Only in the active position a locking between the blade housing 31 and blade 22 can be released, whereby also only then a driving connection is established between the second operating element and the blade 22.

Due to the holding of blade 22 inside the blade housing 31, tissue rests that are carried during retraction of the blade from the tissue are received in the blade housing 31 and enclosed therein. The cleaning and reuse of instrument 12 is thus simpler and safer.

The invention claimed is:

1. A knife cartridge for a surgical instrument, the knife cartridge comprising:
   a cartridge housing configured to be connectable with the instrument;
   a blade housing that is movably supported inside the cartridge housing;
   a blade that is movably supported inside the blade housing;
   a first operating element for moving the blade housing; and
   a second operating element for moving the blade inside the blade housing.

2. The knife cartridge according to claim 1, wherein the cartridge housing comprises a latching means for releasable connection of the cartridge housing with the instrument.

3. The knife cartridge according to claim 2, wherein the latching means is operable by means of the first operating element.

4. The knife cartridge according to claim 1, wherein the blade housing comprises a first locking position in which the blade housing is completely positioned inside the cartridge housing.

5. The knife cartridge according to claim 1, wherein the blade housing comprises a second locking position in which the blade housing partly projects out of the cartridge housing.

6. The knife cartridge according to claim 1, wherein the blade comprises a retraction position in which the blade is fully positioned inside the blade housing and is locked inside the blade housing.

7. The knife cartridge according to claim 1, wherein the blade comprises an extension that can be extended out of the blade housing.

8. The knife cartridge according to claim 1, wherein the first operating element is movably supported on the cartridge housing.

9. The knife cartridge according to claim 1, wherein the first operating element is supported on the cartridge housing along a predefined movement path.

10. The knife cartridge according to claim 8, wherein a pivot lock is effective between the first operating element and the cartridge housing that is configured to allow a pivot movement of the first operating element only in an end position of the movement path.

11. The knife cartridge according to claim 1, wherein the first operating element comprises a coupling for a connection with the blade housing.

12. The knife cartridge according to claim 1, wherein the first operating element and the second operating element can be alternatingly coupled with the blade by means of a transfer mechanism.

13. The knife cartridge according to claim 1, wherein the second operating element can be operatively coupled with the blade by pivot movement of the first operating element.

14. The knife cartridge according to claim 1, wherein an operation lock is effective between the first operating element and the second operating element.

15. The knife cartridge according to claim 1, wherein an insertion feeler is assigned to the first operating element that is configured to lock the operation of the first operating element outside the instrument.

* * * * *